United States Patent
Kwon et al.

(10) Patent No.: US 9,901,899 B2
(45) Date of Patent: Feb. 27, 2018

(54) CARBON DIOXIDE ADSORBENT INCLUDING ALKALI METAL DOUBLE SALTS AND METHODS FOR PREPARING THE SAME

(71) Applicant: Samsung Electronics Co., Ltd., Suwon-si, Gyeonggi-do (KR)

(72) Inventors: Hyuk Jae Kwon, Suwon-si (KR); Soon Chul Kwon, Hwaseong-si (KR); Hyun Chul Lee, Hwaseong-si (KR); Ki-bong Lee, Seoul (KR); Chan Hyun Lee, Seoul (KR); Hee Jin Jang, Seoul (KR)

(73) Assignees: Samsung Electronics Co., LTD., Gyeonggi-Do (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 192 days.

(21) Appl. No.: 14/620,761

(22) Filed: Feb. 12, 2015

(65) Prior Publication Data

US 2015/0306564 A1    Oct. 29, 2015
US 2017/0326526 A9    Nov. 16, 2017

(30) Foreign Application Priority Data

Apr. 28, 2014 (KR) .................. 10-2014-0050953

(51) Int. Cl.
| | |
|---|---|
| *B01J 20/04* | (2006.01) |
| *B01J 20/30* | (2006.01) |
| *B01D 53/02* | (2006.01) |
| *B01D 53/62* | (2006.01) |

(52) U.S. Cl.
CPC ............ *B01J 20/043* (2013.01); *B01D 53/02* (2013.01); *B01D 53/62* (2013.01); *B01J 20/041* (2013.01); *B01J 20/3078* (2013.01); *B01D 2253/112* (2013.01); *B01D 2253/1124* (2013.01); *B01D 2257/504* (2013.01); *Y02C 10/04* (2013.01); *Y02C 10/08* (2013.01)

(58) Field of Classification Search
None
See application file for complete search history.

(56) References Cited

U.S. PATENT DOCUMENTS

| 5,376,293 A | 12/1994 | Johnston |
|---|---|---|
| 6,270,557 B1 | 8/2001 | Millet et al. |
| 6,280,503 B1 | 8/2001 | Mayorga et al. |
| 2006/0286183 A1 | 12/2006 | Gardiner et al. |

(Continued)

FOREIGN PATENT DOCUMENTS

| KR | 2012-0060145 A | 6/2012 |
|---|---|---|
| KR | 2013-0089587 A | 8/2013 |

(Continued)

*Primary Examiner* — Daniel Berns
(74) *Attorney, Agent, or Firm* — Harness, Dickey & Pierce, P.L.C.

(57) ABSTRACT

A carbon dioxide adsorbent may include a double salt having a first metal salt and a second metal salt. The first metal salt may include a first metal selected from Ca, Sr, and Ba. The second metal salt may include a second metal selected from Li, Na, K, Rb, and Cs. The present disclosure also discloses a process for preparing the carbon dioxide adsorbent and a method of separating carbon dioxide using the same.

18 Claims, 8 Drawing Sheets

(56) References Cited

U.S. PATENT DOCUMENTS

| | | |
|---|---|---|
| 2012/0138860 A1 | 6/2012 | Seo et al. |
| 2013/0015399 A1 | 1/2013 | Yu et al. |
| 2013/0199373 A1 | 8/2013 | Kwon et al. |
| 2013/0236726 A1 | 9/2013 | Kwon et al. |
| 2013/0247757 A1 | 9/2013 | Lee et al. |
| 2013/0260990 A1 | 10/2013 | Kwon et al. |
| 2013/0287663 A1* | 10/2013 | Zhang ............... B01D 53/14 423/230 |
| 2014/0174292 A1 | 6/2014 | Kwon et al. |
| 2014/0251135 A1 | 9/2014 | Kwon et al. |
| 2014/0260977 A1 | 9/2014 | Kwon et al. |
| 2014/0350302 A1 | 11/2014 | Ismail et al. |

FOREIGN PATENT DOCUMENTS

| | | |
|---|---|---|
| KR | 2013-0101936 A | 9/2013 |
| KR | 2013-0109061 A | 10/2013 |
| KR | 2013-0109830 A | 10/2013 |
| KR | 2014 0082048 A | 7/2014 |
| KR | 2014-0111549 A | 9/2014 |
| KR | 2014-0113169 A | 9/2014 |
| KR | 2014-0123849 A | 10/2014 |
| WO | WO-2011-110979 A2 | 9/2011 |

\* cited by examiner

CARBON DIOXIDE ADSORBENT INCLUDING ALKALI METAL DOUBLE SALTS AND METHODS FOR PREPARING THE SAME

CROSS-REFERENCE TO RELATED APPLICATION

This application claims priority under 35 U.S.C. § 119 to Korean Patent Application No. 10-2014-0050953, filed in the Korean Intellectual Property Office on Apr. 28, 2014, the entire contents of which is incorporated herein by reference.

BACKGROUND

1. Field

Example embodiments herein relate to a carbon dioxide adsorbent including alkali metal double salts, a process for preparing the same, and a method of separating carbon dioxide using the same.

2. Description of the Related Art

A considerable increase in the concentration of global atmospheric $CO_2$, one of the greenhouse gases, has raised concern about climate change, and has led to increasing efforts in research and development on the control of $CO_2$ emissions. The main $CO_2$ emission sources include fossil fuel-based power plants, vehicles, and manufacturing plants for cement, limestone, hydrogen, ammonia, and the like.

The capture and separation of carbon dioxide from fixed facilities such as various power plants or factories are considered as first measures for the control of $CO_2$ emissions. The capture of carbon dioxide refers to a process of physically or chemically separating $CO_2$ among a gas mixture generated from chemical reactions or combustion of fossil fuels.

In order to capture $CO_2$ by adsorption, carbon materials, zeolites, metal-organic composite materials (MOF), or the like may be used at a low temperature, such as room temperature or lower. Hydrotalcite and metal oxides may be used at a middle-ranged temperature (e.g., at least about 300° C.).

However, a carbon dioxide adsorbent that is used at a low temperature may not be suitable for a facility such as an advanced integrated gasification combined cycle (IGCC) system.

SUMMARY

Some example embodiments relate to a carbon dioxide adsorbent having a novel composition and exhibiting enhanced adsorption/desorption capacity at a relatively high temperature.

Some example embodiments relate to a process for preparing the carbon dioxide adsorbent.

Some example embodiments relate to a method of separating carbon dioxide that includes using the carbon dioxide adsorbent.

According to one example embodiment, a carbon dioxide adsorbent may include a double salt having a first metal salt and a second metal salt, the first metal salt including a first metal selected from Ca, Sr, and Ba, and the second metal salt including a second metal selected from Li, Na, K, Rb, and Cs.

The first metal salt may include an oxide and optionally a carbonate.

The second metal salt may include a carbonate and optionally a hydrogen carbonate.

The double salt may have a mole ratio of the second metal to the first metal (the second metal/the first metal) being greater than or equal to about 0.01 and less than or equal to about 0.36.

The double salt may also have a mole ratio of the second metal to the first metal (the second metal/the first metal) being greater than or equal to about 0.03 and less than or equal to about 0.3.

The carbon dioxide adsorbent may have a $CO_2$ adsorption efficiency of greater than or equal to about 40% as determined by thermogravimetric analysis for $CO_2$ adsorption at a temperature of about 600° C. and a gas pressure of about 1 bar.

The carbon dioxide adsorbent may show a desorption efficiency of about 100% within 10 minutes in the absence of water at a temperature of about 800° C. and a gas pressure of about 1 bar.

According to another example embodiment, a process for preparing a carbon dioxide adsorbent (that includes a double salt having a first metal salt and a second metal salt, the first metal salt including a first metal selected from Ca, Sr, and Ba, and the second metal salt including a second metal selected from Li, Na, K, Rb, and Cs) may include adding a precursor of the second metal salt to a solution of a precursor of the first metal salt while stirring to obtain a slurry; aging the slurry by stirring the slurry for more than three hours to; separating a solid component from the slurry; optionally drying the solid component; and heating the solid component being optionally dried to obtain the carbon dioxide adsorbent including the double salt.

The double salt may have a mole ratio of the second metal to the first metal (the second metal/the first metal) being greater than or equal to about 0.01 and less than or equal to about 0.36.

The process may further include washing the separated double salt with water so that the double salt has a mole ratio of the second metal to the first metal (the second metal/the first metal) being greater than or equal to about 0.01 and less than or equal to about 0.36.

The precursor of the second metal salt may include $Li_2CO_3$, $Na_2CO_3$, $K_2CO_3$, $Rb_2CO_3$, $Cs_2CO_3$, or a hydrate thereof.

The precursor of the first metal salt may include $CaNO_3$, $SrNO_3$, $BaNO_3$, or a hydrate thereof.

The precursor of the second metal salt may be added for the mole ratio of the second metal to the first metal to be about 1.5 to about 12.

The aging of the solid component may be carried out at a temperature of less than or equal to about 60° C., (e.g., about 35° C. or lower) for less than 12 hours.

The drying may be carried out at a temperature between 25° C. and 120° C.

The heating may be carried out at a temperature of greater than or equal to about 650° C. in air.

According to yet another example embodiment, a method of separating carbon dioxide may include bringing an input gas stream (e.g., gas mixture) containing carbon dioxide into contact with a carbon dioxide adsorbent that includes a double salt having a first metal salt and a second metal salt, the first metal salt including a first metal selected from Ca, Sr, and Ba, and the second metal salt including a second metal selected from Li, Na, K, Rb, and Cs.

The first metal salt may include an oxide and optionally a carbonate.

The second metal salt may include a carbonate and optionally a hydrogen carbonate.

The double salt may have a mole ratio of the second metal to the first metal (the second metal/the first metal) being greater than or equal to about 0.01 and less than or equal to about 0.36.

The method may further include heat-treating the carbon dioxide adsorbent at a temperature of about 200° C. to about 900° C., optionally under a reduced pressure, to desorb the carbon dioxide.

The gas mixture may further include at least one gas selected from hydrogen, nitrogen, and methane.

The gas mixture may be in contact with the carbon dioxide adsorbent at a temperature of about 500° C. to about 700° C.

According to the aforementioned embodiments, the carbon dioxide adsorbent may adsorb carbon dioxide with increased efficiency even at a relatively high temperature. The carbon dioxide adsorbent may exhibit higher adsorption efficiency at a relatively high temperature and, at the same time, may show a desorption efficiency of 100% even in the absence of water and such desorption may be accomplished within a relatively short time.

DETAILED DESCRIPTION

It will be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It will be understood that, although the terms first, second, third, etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of example embodiments.

Spatially relative terms, e.g., "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms, "comprises," "comprising," "includes," and/or "including," if used herein, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Unless specifically mentioned to the contrary, the term "double salt" used herein refers to a salt containing at least two cations or anions. The double salt is obtained by a combination of at least two different salts being crystallized in the same regular ionic lattice. Properties of the double salt are not the same as the properties of the single salts constituting it.

Unless specifically mentioned to the contrary, the term "input gas stream" used herein refers to a gas stream prior to passing through an adsorbent region or prior to initial contact with an adsorbent.

A carbon dioxide adsorbent according to an example embodiment may include a double salt having a first metal salt and a second metal salt, the first metal salt including a first metal selected from Ca, Sr, and Ba, and the second metal salt including a second metal selected from Li, Na, K, Rb, and Cs. The first metal salt may include an oxide and optionally a carbonate. The first metal salt may further include a hydroxide. For example, the first metal salt may include $CaO$, $CaCO_3$, $Ca(OH)_2$, $SrO$, $SrCO_3$, $Sr(OH)_2$, $BaO$, $BaCO_3$, $Ba(OH)_2$, a hydrate thereof, or a combination thereof. The second metal salt may include a carbonate, a hydrogen carbonate, a combination thereof, or a hydrate thereof. For example, the second metal salt may include $Li_2CO_3$, $Na_2CO_3$, $K_2CO_3$, $Rb_2CO_3$, $Cs_2CO_3$, $LiHCO_3$, $NaHCO_3$, $KHCO_3$, $RbHCO_3$, $CsHCO_3$, or a hydrate thereof.

The double salt may include hydrated water. Without wishing to be bound by any theory, in the double salt according to the non-limiting embodiments, the hydrated water may contribute to formation of the hydroxide of the first metal salt. In its XRD spectrum, the double salt may have peaks corresponding to the salts included therein, respectively.

In an example embodiment, the double salt may be represented by Chemical Formula 1.

$$(M^2{}_2CO_3)_n(M^1CO_3)_p(M^1O)_{1-p} \cdot xH_2O \quad \text{[Chemical Formula 1]}$$

In the above Formula, $M^1$ is the first metal, $M^2$ is the second metal, n is greater than or equal to 0.01 and less than 0.36, for example, between 0.03 and 0.3, p is greater than or equal to 0 and less than 1, and x is a number representing a degree of hydration of the double salt.

In an example embodiment, the hydrated water in Chemical Formula 1 and the oxide of the first metal may be confirmed by the presence of the hydroxy peak of the first metal in the XRD spectrum.

The double salt may have a mole ratio of the second metal to the first metal (the second metal/the first metal) of greater than or equal to about 0.01 and less than or equal to about 0.36. For example, the double salt may have a mole ratio of the second metal to the first metal (the second metal/the first metal) that ranges from about 0.03 to about 0.3, or ranges from about 0.04 to about 0.2. When the mole ratio of the second metal to the first metal (the second metal/the first metal) is within the aforementioned range, the carbon dioxide adsorbent may exhibit significantly improved adsorption efficiency. The double salt may have a specific surface area of less than or equal to about 5 m$^2$/g, for example, from 1.5 m$^2$/g to 3.5 m$^2$/g, as determined by a BET method.

The carbon dioxide adsorbent including the aforementioned double salt may exhibit significantly improved adsorption efficiency at a relatively high temperature. For example, the carbon dioxide adsorbent may have a CO$_2$ adsorption efficiency of greater than or equal to about 40%, greater than or equal to about 42%, or greater than or equal to about 45%, as determined by a thermogravimetric analysis for CO$_2$ adsorption at a temperature of about 600° C. and a gas pressure of about 1 bar. The carbon dioxide adsorbent may have a CO$_2$ adsorption efficiency of greater than or equal to about 9.1 mmol/g, for example, greater than or equal to about 9.5 mmol/g, or greater than or equal to about 10.25 mmol/g, when converted to a unit of mmol/g. In addition, the carbon dioxide adsorbent may show a desorption efficiency of about 100% within 10 minutes in the absence of water at a temperature of about 800° C. and a gas pressure of about 1 bar.

The aforementioned double salt may be synthesized by the following method with high reproducibility. In addition, the carbon dioxide adsorbent including the aforementioned double salt may exhibit enhanced CO$_2$ adsorption capacity in comparison with a simple compound including the same salts. For example, the carbon dioxide adsorbent including the double salt having calcium (Ca) as the first metal includes $M^2{}_2CO_3$ together with CaO and CaCO$_3$. The carbon dioxide adsorbent including such a double salt may show significantly improved adsorption efficiency at a relatively high temperature (e.g., at about 600° C. or higher).

The carbon dioxide adsorbent including the aforementioned double salt may accomplish greatly enhanced results in terms of desorption efficiency/capacity. For example, the carbon dioxide adsorbent including CaO and the like may require a long time for desorption in the absence of water, and this may be a serious disadvantage for use as the carbon dioxide adsorbent. By contrast, in case of the carbon dioxide adsorbent including CaO, SrO, or BaO in the form of a double salt, the carbon dioxide being adsorbed may be completely desorbed (accomplish 100% desorption) within a shortened period of time even in the absence of water. Without wishing to be bound by any theory, this may result from the following reasons. In general, CaO adsorbs the carbon dioxide via natural mineralization represented as below, and thus the desorption may be difficult in the absence of water.

$$CaO\ (s) + CO_2\ (g) \longleftrightarrow CaCO_3\ (s).$$

By contrast, in case of the carbon dioxide adsorbent including the double salt, the desorption of the carbon dioxide may easily occur even in the absence of water as the adsorption/desorption reaction proceeds as below.

$$Na_2CO_3\ (s) + CaO\ (s) + CO_2\ (g) \longleftrightarrow Na_2Ca(CO_3)_2\ (s).$$

In another example embodiment, a process for preparing the aforementioned carbon dioxide adsorbent may include adding a precursor of a second metal salt to a solution of a precursor of a first metal salt while stirring to obtain a slurry; stirring the slurry for more than three hours to age the same; separating a solid component from the slurry; optionally drying the solid component; and heat-treating the solid component to obtain a carbon dioxide adsorbent including the double salt.

The carbon dioxide adsorbent thus prepared may have a CO$_2$ adsorption efficiency of greater than or equal to about 40% as determined by thermogravimetric analysis for CO$_2$ adsorption at a temperature of about 600° C. and a gas pressure of about 1 bar. The process may further include washing the separated double salt with water so that the double salt has a desired mole ratio of the second metal to the first metal.

The types and the amounts of the first metal and the second metal in the double salt may be the same as set forth above.

The ratio between the first metal and the second metal in the double salt may be controlled by adjusting the ratio between the precursor of the first metal salt and the precursor of the second metal salt, the washing time, and the like.

The precursor of the second metal salt may include Li$_2$CO$_3$, Na$_2$CO$_3$, K$_2$CO$_3$, Rb$_2$CO$_3$, Cs$_2$CO$_3$, or a hydrate thereof, but it is not limited thereto. The precursor of the first metal salt may include CaNO$_3$, SrNO$_3$, BaNO$_3$, or a hydrate thereof, but it is not limited thereto.

The first metal salt may be dissolved in water (e.g., distilled water) to prepare an aqueous solution. While the aqueous solution thus obtained is stirred vigorously, the precursor of the second metal salt is gradually added thereto over a predetermined time, e.g., for 30 minutes or longer, for 40 minutes or longer, or for 50 minutes or longer. The temperature of the aqueous solution may be controlled to be in the range of room temperature to about 80° C., for example, greater than or equal to about 20° C., greater than or equal to about 25° C., greater than or equal to about 30° C., greater than or equal to about 40° C., or greater than or equal to about 60° C., but it is not limited thereto. In the slurry, the mole ratio of the second metal to the first metal may be greater than or equal to about 1, for example, greater than or equal to about 1.2, greater than or equal to about 1.3, greater than or equal to about 1.4, greater than or equal to about 1.5, greater than or equal to about 2.0, greater than or equal to about 3.0, greater than or equal to about 4.0, or greater than or equal to about 5.0. In the slurry, the mole ratio of the second metal to the first metal may be less than about 24, for example, less than about 23, less than about 22, less than about 21, less than about 20, less than about 19, less than about 18, less than about 17, less than about 16, less than about 15, less than about 14, less than about 13, less than or equal to about 12, less than or equal to about 11, less than or equal to about 10, less than or equal to about 9, less than or equal to about 8, or less than or equal to about 7. For example, in the slurry, the mole ratio of the second metal to the first metal may be controlled to range from about 1.5 to about 6. When the mole ratio of the second metal to the first metal is within the aforementioned range, the ratio of the second metal to the first metal in the double salt may be greater than or equal to about 0.01 and less than 0.36.

The slurry thus prepared is stirred for a time greater than 3 hours (e.g., for 4 hours or longer, or for 5 hours or longer) to be aged. The aging temperature may be controlled to be less than or equal to about 60° C., or less than or equal to about 35° C., for example, from about 20° C. to about 60° C., from about 15° C. to about 35° C., or from about 20° C. to about 30° C. The slurry thus prepared is aged for less than about 12 hours, for example, less than or equal to about 11 hours, or less than or equal to about 10 hours. In an example embodiment, the slurry is aged for about 6 to 11 hours, or for about 8 to 10 hours. When the aging time and the aging temperature are within the aforementioned ranges, the carbon dioxide adsorbent including the double salt thus synthesized may exhibit greatly enhanced adsorption capacity (e.g. greater than or equal to about 40%).

The solid component formed in the aged slurry is separated therefrom for example by filtration or centrifugation. If desired, the separated solid may be washed with water. As mentioned above, controlling the amount of the precursor of the first metal salt and the precursor of the second metal salt and washing the separated solid component with water makes it possible to control the mole ratio between the first metal and the second metal in the double salt within the aforementioned range.

The separated (and optionally washed) solid component may be dried for example at a temperature higher than room temperature, for example, at a temperature of greater than or equal to about 25° C., greater than or equal to about 60° C., greater than or equal to about 80° C., greater than or equal to about 90° C., greater than or equal to about 100° C., or greater than or equal to about 110° C. The atmosphere and the time for the drying are not particularly limited and may be selected appropriately.

The dried solid component is heat-treated (i.e., calcined or activated) at a temperature of greater than or equal to about 600° C. in air.

When the aforementioned synthesis conditions are followed, the double salt thus prepared may exhibit substantially the same level of adsorption capacity when it is used as the carbon dioxide adsorbent. In other words, the aforementioned process has a relatively high level of reproducibility of synthesis.

In another example embodiment, the method of separating carbon dioxide may include contacting a gas mixture including carbon dioxide with a carbon dioxide adsorbent including a double salt having a first metal salt and a second metal salt, the first metal salt including a first metal selected from Ca, Sr, and Ba, and the second metal salt including a second metal selected from Li, Na, K, Rb, and Cs.

Details of the carbon dioxide adsorbent may be the same as set forth above. The gas mixture including carbon dioxide may be an input gas stream including carbon dioxide. Besides carbon dioxide, the gas mixture may further include hydrogen, a hydrocarbon, nitrogen, or a combination thereof. The carbon dioxide adsorbent may be brought into contact with the gas mixture at a temperature of greater than or equal to about 25° C., and for example, from about 30° C. to about 650° C., from about 450° C. to about 650° C., or from about 500° C. to about 650° C. The carbon dioxide adsorbent may exhibit a high level of adsorption capacity not only at a low temperature but also at a relatively high temperature.

The method of separating carbon dioxide may further include heat-treating the carbon dioxide adsorbent at a temperature of about 50° C. to about 900° C., for example of about 200° C. to about 850° C., under a reduced pressure to desorb carbon dioxide, and emitting the same. The desorption pressure is not particularly limited, but is in a range of less than or equal to about 1000 Pa, and specifically about 700 Pa to about 50 Pa, for example, about 100 Pa.

Figure 8:
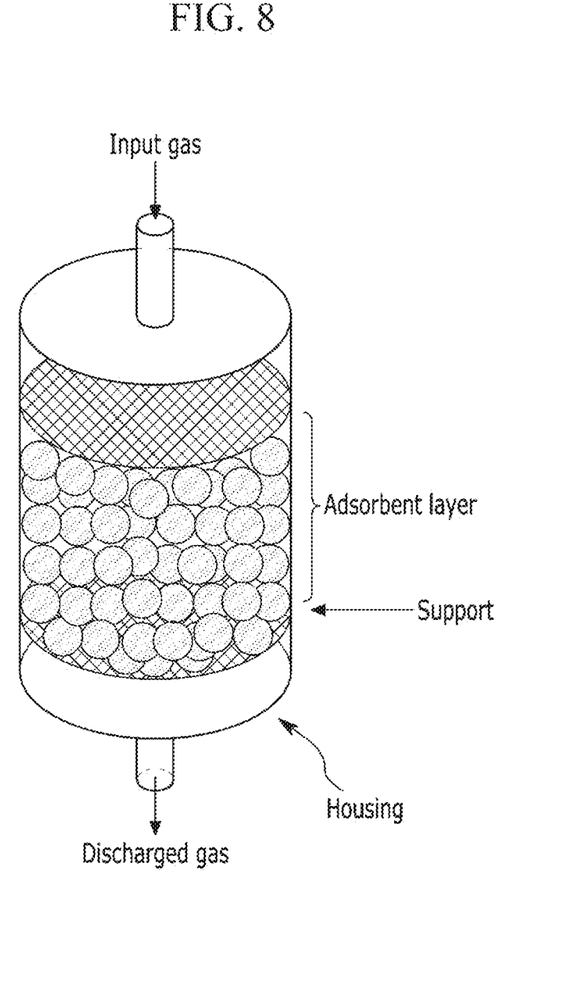
FIG. 8 illustrates a schematic view of a carbon dioxide capture module according to an example embodiment.

The carbon dioxide adsorbent may be used in the form of a carbon dioxide capture module. In a non-limiting example as shown in FIG. 8, the carbon dioxide capture module includes an adsorption layer including the carbon dioxide adsorbent, a support plate holding the adsorption layer, and a housing including an inlet for an input gas stream and an outlet for the treated gas stream. Details of the carbon dioxide adsorbent may be the same as set forth above. The thickness of the adsorption layer is not particularly limited, but may be greater than or equal to about 0.2 cm, and specifically from about 0.5 cm to about 3 cm. The support plate may be made of any materials as long as it may support the adsorbent while allowing the flow of the input gas. Examples of the material may include quartz wool or the like. Materials and shapes of the housing for the module are not particularly limited, but may be selected as needed. By way of non-limiting examples, the housing may be made of stainless steel, copper pipe, or quartz pipe, and may have a shape of cylinder, a prism, a square column, or the like.

The input gas stream may further include at least one gas selected from hydrogen, nitrogen, and hydrocarbons (e.g., methane). The composition of the input gas stream is not particularly limited, but may be appropriately selected as needed. For example, the input gas stream may include carbon dioxide and nitrogen like in a flue gas generated from a fossil fuel power plant. The input gas stream may include carbon dioxide and hydrogen like in a flue gas generated from an integrated gasification combined cycle (IGCC) power plant. The input gas stream may include carbon dioxide and methane like in a gas generated from a natural gas well. The flow rate of supplying the input gas stream is not particularly limited, but may be appropriately selected as desired. For example, the flow rate may be less than or equal to about 1000 ml/min, and specifically, less than or equal to about 500 ml/min.

The carbon dioxide adsorbent may be prepared via the aforementioned synthesis process with a relatively high level of reproducibility. In addition, the carbon dioxide adsorbent may exhibit a relatively high level of $CO_2$ adsorption capacity at a relatively high temperature. In addition, desorption may easily proceed at a relatively low temperature (of about 800° C. or lower) to reach 100% desorption efficiency. Therefore, the carbon dioxide adsorbent of the foregoing embodiments may hold great potential for use in the advanced IGCC that is currently developed in order to exclude the use of a cooler or a re-heater.

The following examples illustrate various embodiments in more detail. However, it should be understood that the following are merely examples, and this disclosure is not limited thereto.

EXAMPLES

Preparation Example 1

7.46 g of $Ca(NO_3)_2 \cdot 4H_2O$ is dissolved in 100 mL of distilled water to prepare an aqueous solution. While the aqueous solution is vigorously stirred, 10 g of $Na_2CO_3$ is gradually added at room temperature over 60 min to obtain a slurry (mole ratio of Na/Ca=about 6). The slurry thus obtained is stirred at room temperature for 9 h to be aged.

The aged slurry is filtered to separate solids therefrom. The separated solids are washed with water, dried in a vacuum oven at a temperature of about 110° C., and then is calcined (i.e. activated) in air at a temperature of about 800° C. to obtain a double salt including CaO, $CaCO_3$, $Na_2CO_3$, $Na_2CO_3 \cdot H_2O$, and partially $Ca(OH)_2$ (see an XRD spectrum of FIG. 1).

Figure 1:
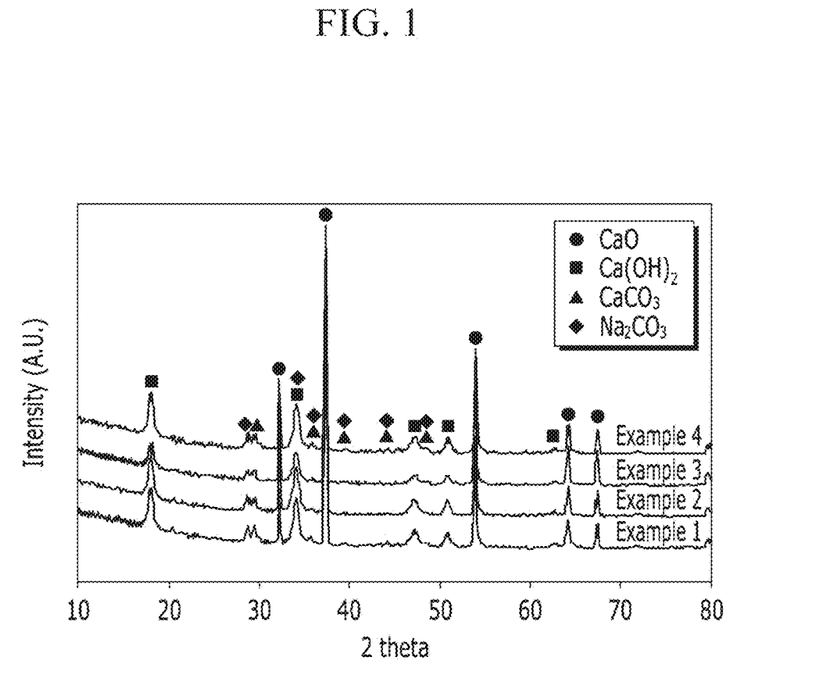
FIG. 1 shows X-ray diffraction spectrums of the double salts prepared in Preparation Examples 1 to 4, respectively.
Figure 2:
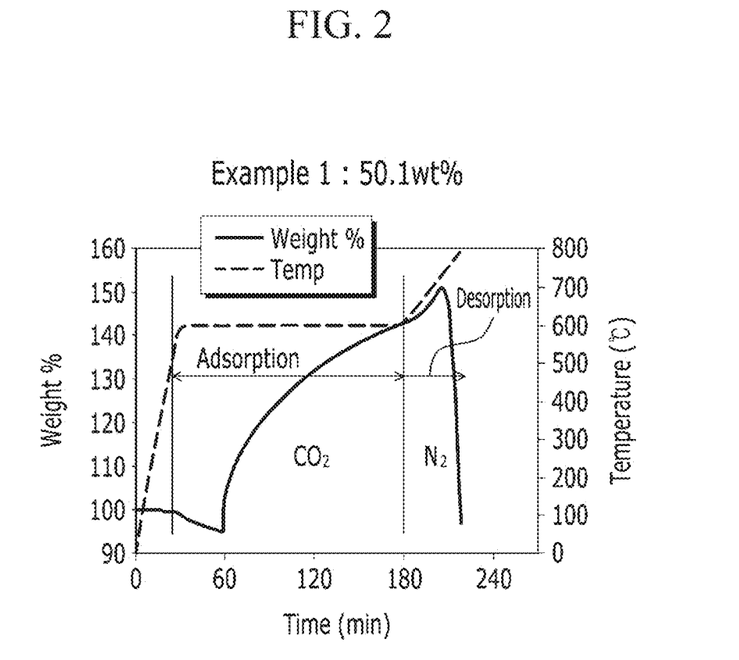
FIG. 2 to FIG. 5 are views illustrating the results of a $CO_2$ adsorption experiments in accordance with Examples 1 to 4, respectively.
Figure 3:
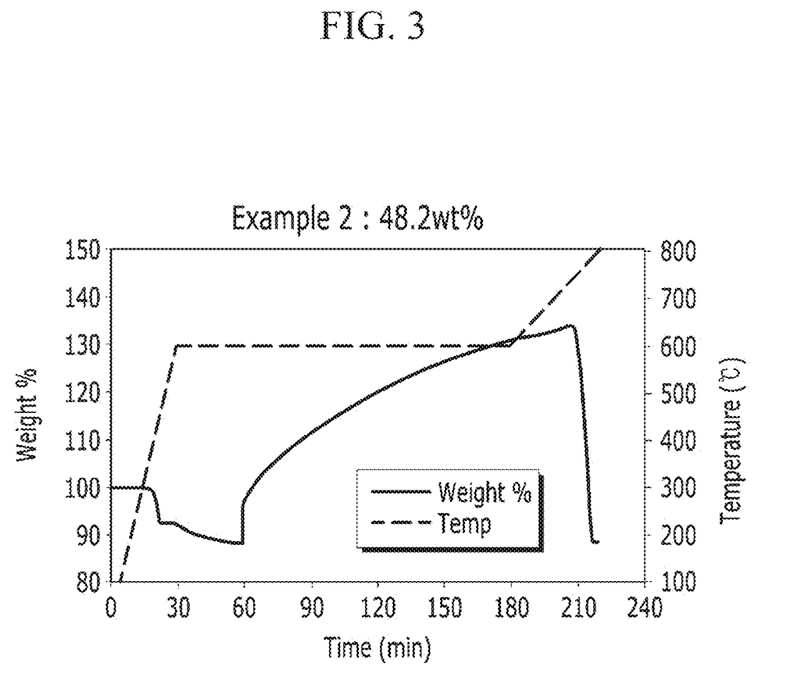
Figure 4:
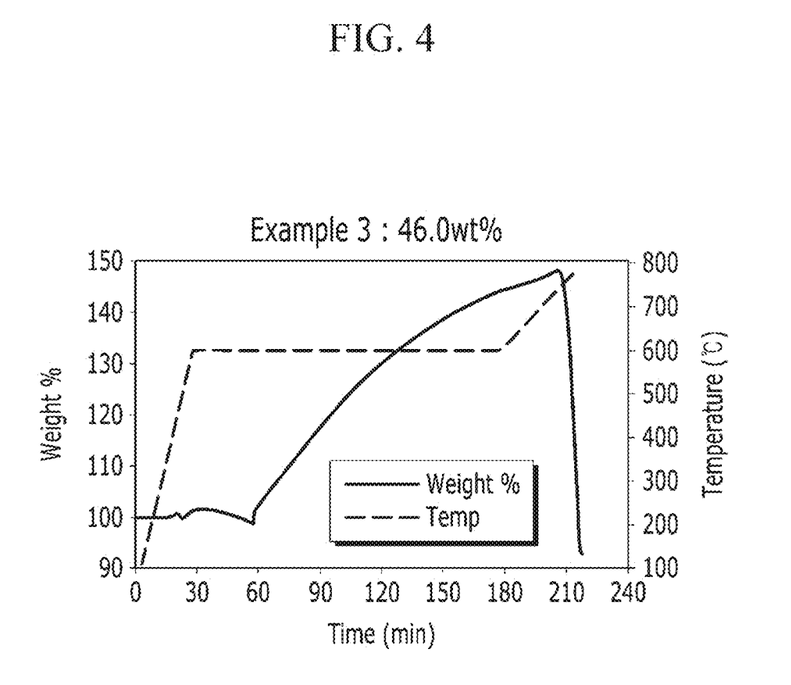
Figure 5:
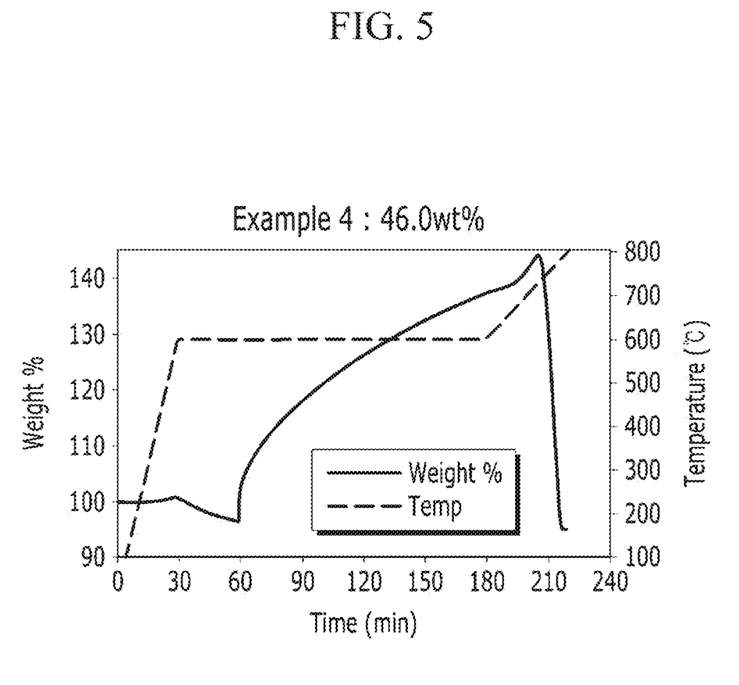

An X-ray diffraction (XRD) analysis is made for the double salt thus prepared. The X-ray diffraction analysis is performed using a Cu Kα ray as a light source, and is operated at 40 kV and 40 mA at a scan speed of 0.005° per second. The results are shown in FIG. 1.

An inductively coupled plasma analysis is conducted using Shimadzu ICPS-8100 to calculate the mole ratio of Na/Ca in the double salt thus prepared. The results are shown in Table 1.

Figure 7:
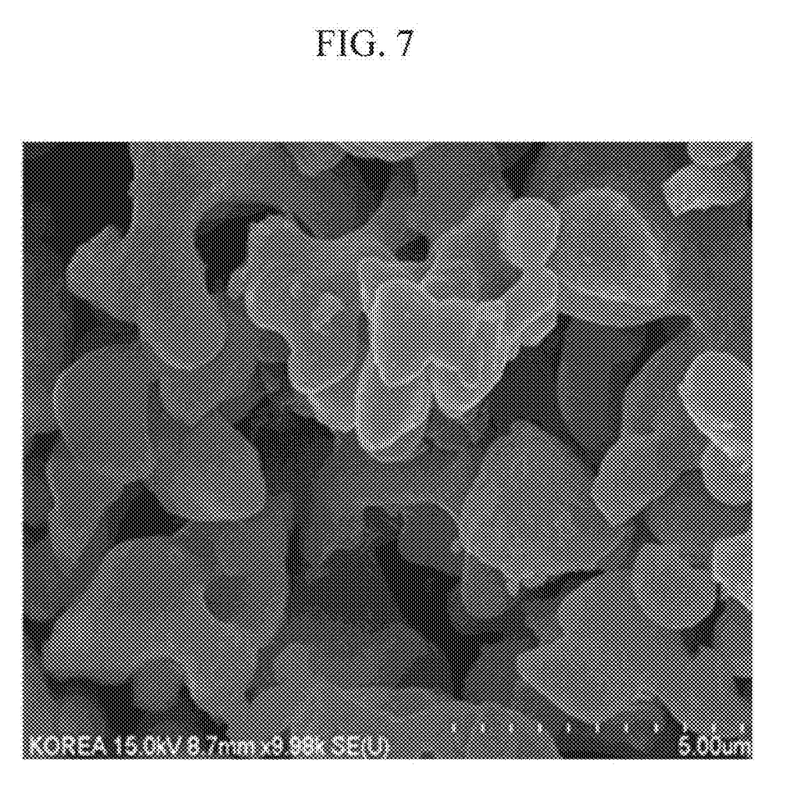
FIG. 7 is a scanning electron microscopic image for the double salt prepared in Preparation Example 1.

A SEM analysis is made using Hitachi S-4300 equipment for the double salt thus prepared, and the results are shown in FIG. 7.

Preparation Example 2

A double salt is prepared in the same manner as set forth in Preparation Example 1, except that while the aqueous solution is vigorously stirred, 5 g of $Na_2CO_3$ is gradually added at room temperature over 60 min to obtain a slurry (mole ratio of Na/Ca=about 3).

An X-ray diffraction (XRD) analysis is made for the double salt thus prepared. The X-ray diffraction analysis is performed using a Cu Kα ray as a light source, and is operated at 40 kV and 40 mA at a scan speed of 0.005° per second. The results are shown in FIG. 1. The results of FIG. 1 confirm that the double salt thus prepared includes CaO, $CaCO_3$, $Na_2CO_3$, $Na_2CO_3 \cdot H_2O$, and partially $Ca(OH)_2$.

An inductively coupled plasma analysis is conducted using Shimadzu ICPS-8100 equipment to calculate the mole ratio of Na/Ca in the double salt thus prepared. The results are shown in Table 1.

Preparation Example 3

A double salt is prepared in the same manner as set forth in Preparation Example 1, except that while the aqueous solution is vigorously stirred, 2.5 g of $Na_2CO_3$ is gradually added at room temperature over 60 min to obtain a slurry (mole ratio of Na/Ca=about 1.5).

An X-ray diffraction (XRD) analysis is made for the double salt thus prepared. The X-ray diffraction analysis is performed using a Cu Kα ray as a light source, and is operated at 40 kV and 40 mA at a scan speed of 0.005° per second. The results are shown in FIG. 1. The results of FIG. 1 confirm that the double salt thus prepared includes CaO, $CaCO_3$, $Na_2CO_3$, $Na_2CO_3 \cdot H_2O$, and partially $Ca(OH)_2$.

An inductively coupled plasma analysis is conducted using Shimadzu ICPS-8100 equipment to calculate the mole ratio of Na/Ca in the double salt thus prepared. The results are shown in Table 1.

Preparation Example 4

A double salt is prepared in the same manner as set forth in Preparation Example 1 except that while the aqueous solution is vigorously stirred, 20 g of $Na_2CO_3$ is gradually added at room temperature over 60 min to obtain a slurry (mole ratio of Na/Ca=about 12).

An X-ray diffraction (XRD) analysis is made for the double salt thus prepared. The X-ray diffraction analysis is performed using a Cu Kα ray as a light source, and is operated at 40 kV and 40 mA at a scan speed of 0.005° per second. The results are shown in FIG. 1. The results of FIG. 1 confirm that the double salt thus prepared includes CaO, $CaCO_3$, $Na_2CO_3$, $Na_2CO_3 \cdot H_2O$, and partially $Ca(OH)_2$.

An inductively coupled plasma analysis is conducted using Shimadzu ICPS-8100 equipment to calculate the mole ratio of Na/Ca in the double salt thus prepared. The results are shown in Table 1.

Preparation Example 5

A double salt is prepared in the same manner as set forth in Preparation Example 1, except that the slurry is aged for 6 h at room temperature (mole ratio of Na/Ca=about 6).

Comparative Preparation Example 1

A double salt is prepared in the same manner as set forth in Preparation Example 1, except that while the aqueous solution is vigorously stirred, 40 g of $Na_2CO_3$ is gradually added at room temperature over 60 min to obtain a slurry (mole ratio of Na/Ca=about 24).

An inductively coupled plasma analysis is conducted using Shimadzu ICPS-8100 equipment to calculate the mole ratio of Na/Ca in the double salt thus prepared. The results are shown in Table 1.

The results of the XRD analysis confirm that the double salt thus prepared is a calcium-sodium based double salt primarily including CaO, $Ca(OH)_2$, $Na_2CO_3$, and $CaCO_3$.

Comparative Preparation Example 2

A double salt is prepared in the same manner as set forth in Preparation Example 1, except excluding the room temperature aging step (mole ratio of Na/Ca=about 6).

Comparative Preparation Example 3

A double salt is prepared in the same manner as set forth in Preparation Example 1, except the slurry is aged for three h at room temperature (mole ratio of Na/Ca=about 6).

Comparative Preparation Example 4

A double salt is prepared in the same manner as set forth in Preparation Example 1, except the slurry is aged for 12 h at room temperature (mole ratio of Na/Ca=about 6).

Comparative Preparation Example 5

A double salt is prepared in the same manner as set forth in Preparation Example 1, except the slurry is aged for 15 h at room temperature (mole ratio of Na/Ca=about 6).

Comparative Preparation Example 6

A double salt is prepared in the same manner as set forth in Preparation Example 1, except the slurry is aged for 18 h at room temperature (mole ratio of Na/Ca=about 6).

Comparative Preparation Example 7

A double salt including Mg and Na is prepared in the same manner as set forth in Preparation Example 1, except the slurry is obtained by gradually mixing $Na_2CO_3$ and $Mg(NO_3)_2.4H_2O$ at a mole ratio of 6 (mole ratio of Na/Mg=about 6).

An inductively coupled plasma analysis is conducted using Shimadzu ICPS-8100 equipment to calculate the mole ratio of Na/Mg in the double salt thus prepared. The results are shown in Table 1.

Figure 6:
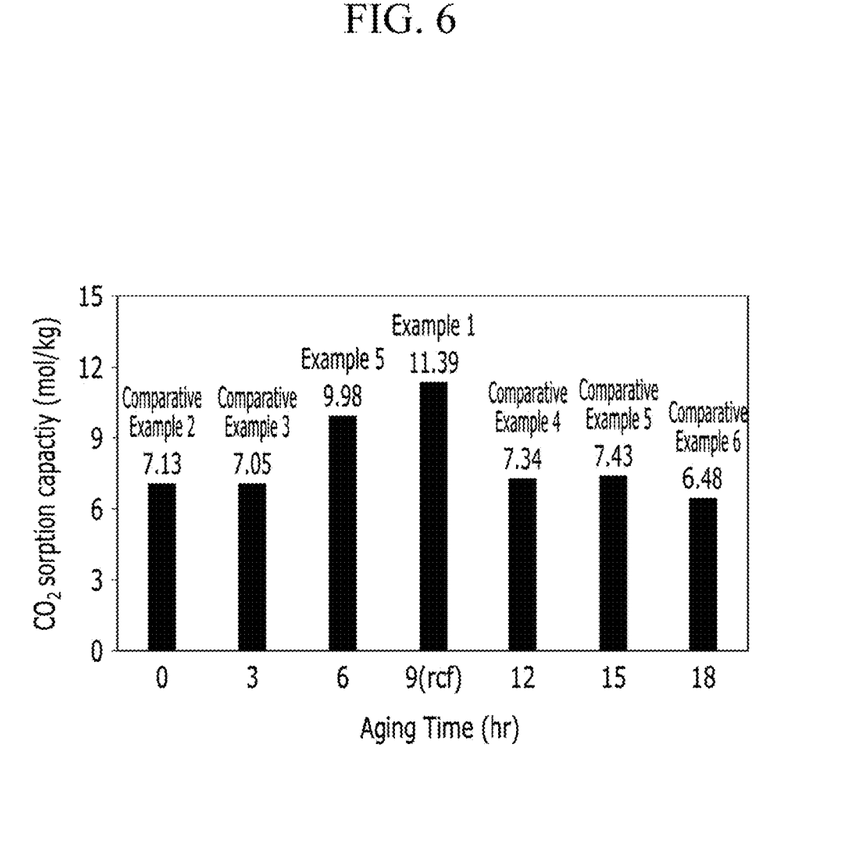
FIG. 6 illustrates the results of $CO_2$ adsorption tests in accordance with Example 1, Example 5, and Comparative Examples 2 to 6.

Carbon Dioxide Adsorption and Desorption Experiments:

$CO_2$ adsorption and desorption experiments are conducted under the following conditions using a carbon dioxide adsorbent (Example 1) including the double salt of Preparation Example 1, a carbon dioxide adsorbent (Example 2) including the double salt of Preparation Example 2, a carbon dioxide adsorbent (Example 3) including the double salt of Preparation Example 3, a carbon dioxide adsorbent (Example 4) including the double salt of Preparation Example 4, a carbon dioxide adsorbent (Example 5) including the double salt of Preparation Example 5, carbon dioxide adsorbents (Comparative Examples 1 to 6) each including the double salt of Comparative Preparation Examples 1 to 6, a carbon dioxide adsorbent (Comparative Example 7) including the double salt of Comparative Preparation Example 7, and a carbon dioxide adsorbent (Comparative Example 8) including CaO manufactured by Aldrich Co., Ltd. The results of Examples 1 to 4 are respectively shown in FIG. 2 to FIG. 5, and the results of Example 1 and Comparative Examples 2 to 7 are shown in FIG. 6. For each of the examples and the comparative examples, the results of TGA adsorption capacity are compiled in Table 1.

Gas Composition: 100% $CO_2$ (Pretreatment: 100% nitrogen)

Adsorption conditions: 600° C., 1 bar, 100% $CO_2$
Desorption conditions: 800° C., 1 bar, 100% $N_2$ In the TGA experiment, the adsorption capacity is evaluated in the following manner: The increased weight by $CO_2$ adsorption is calculated based on the initial weight of the adsorbent.

TABLE 1

| | Double salt composition | Na/Ca mole ratio (ICP) | TGA mmol/g | TGA wt % |
|---|---|---|---|---|
| Example 1 | NaCa double salt | 0.17 | 11.39 | 50.1 |
| Example 2 | NaCa double salt | 0.08 | 10.95 | 48.2 |
| Example 3 | NaCa double salt | 0.05 | 10.45 | 46.0 |
| Example 4 | NaCa double salt | 0.15 | 9.6 | 42.2 |
| Comp. Example 1 | NaCa double salt | 0.36 | 7.81 | 34.4 |
| Comp. Example 2 | NaCa double salt | — | 7.13 | 31.4 |
| Comp. Example 3 | NaCa double salt | — | 7.05 | 31.0 |
| Example 5 | NaCa double salt | — | 9.98 | 43.9 |
| Comp. Example 4 | NaCa double salt | — | 7.34 | 32.3 |
| Comp. Example 5 | NaCa double salt | — | 7.43 | 32.7 |
| Comp. Example 6 | NaCa double salt | — | 6.48 | 28.5 |
| Comp. Example 7 | NaMg double salt | 0.95 | 3.48 | 15.3 |
| Comp. Example 8 | commercial CaO | — | 9.0 | 39.6 |

The results of Table 1 and FIG. 2 to FIG. 5 confirm that the carbon dioxide adsorbents of Examples 1 to 5 may have a $CO_2$ adsorption capacity that is significantly higher (for example by about 40%) than the carbon dioxide adsorbents of the comparative examples. In addition, the carbon dioxide adsorbent of Examples 1 to 5 may accomplish desorption of 100% within a short period of time.

While various example embodiments are disclosed herein, it is to be understood that the present disclosure is not limited to the disclosed embodiments, but, on the contrary, is intended to cover various modifications and equivalent arrangements included within the spirit and scope of the appended claims.

What is claimed is:

1. A carbon dioxide adsorbent comprising: a double salt including a first metal salt and a second metal salt, the first metal salt including CaO, $CaCO_3$, and/or $Ca(OH)_2$, and the second metal salt including $Na_2CO_3$ and/or $Na_2CO_3.H_2O$, wherein the carbon dioxide adsorbent does not include MgO; and wherein the Na:Ca mole ratio is greater than or equal to about 0.01 and less than about 0.36.

2. The carbon dioxide adsorbent of claim 1, wherein the first metal salt comprises CaO.

3. The carbon dioxide adsorbent of claim 1, wherein the second metal salt comprises $Na_2CO_3$.

4. The carbon dioxide adsorbent of claim 1, wherein the Na:Ca mole ratio is greater than or equal to about 0.03 and less than or equal to about 0.3.

5. The carbon dioxide adsorbent of claim 1, wherein the carbon dioxide adsorbent has a $CO_2$ adsorption efficiency of greater than or equal to about 40% as determined by thermogravimetric analysis for $CO_2$ adsorption at a temperature of about 600° C. and a gas pressure of about 1 bar.

6. The carbon dioxide adsorbent of claim 1, wherein the carbon dioxide adsorbent shows a desorption efficiency of about 100% within 10 minutes in the absence of water at a temperature of about 800° C. and a gas pressure of about 1 bar.

7. A process for preparing a carbon dioxide adsorbent comprising a double salt including a first metal salt and a second metal salt, the first metal salt including CaO, $CaCO_3$, and/or $Ca(OH)_2$, and the second metal salt including $Na_2CO_3$ and/or $Na_2CO_3.H_2O$, wherein the carbon dioxide adsorbent does not include MgO, the process comprising:
adding a precursor of the second metal salt to a solution of a precursor of the first metal salt while stirring to obtain a slurry;
aging the slurry by stirring the slurry for more than three hours;
separating a solid component from the slurry; and
heat-treating the solid component to obtain the carbon dioxide adsorbent including the double salt, wherein the Na:Ca mole ratio obtained from the heat-treating is greater than or equal to about 0.01 and less than about 0.36,
wherein a mole ratio of the second metal to the first metal of the carbon dioxide adsorbent obtained from the heat-treating is greater than or equal to about 0.01 and less than about 0.36.

8. The process for preparing a carbon dioxide adsorbent of claim 7, wherein the aging is carried out at a temperature of about 20° C. to 60° C. for less than 12 hours.

9. The process for preparing a carbon dioxide adsorbent of claim 7, wherein the precursor of the second metal salt comprises $Na_2CO_3$ or a hydrate thereof.

10. The process for preparing a carbon dioxide adsorbent of claim 7, wherein the precursor of the first metal salt comprises $CaNO_3$ or a hydrate thereof.

11. The process for preparing a carbon dioxide adsorbent of claim 7, wherein the precursor of the second metal salt is added in such an amount that the Na:Ca mole ratio is about 1.5 to about 12.

12. The process for preparing a carbon dioxide adsorbent of claim 7, further comprising:
    drying the solid component at a temperature between 25° C. and 120° C. prior to the heat-treating.

13. The process for preparing a carbon dioxide adsorbent of claim 7, wherein the heat-treating is carried out at a temperature of greater than or equal to about 650° C. in air.

14. A method of separating carbon dioxide, comprising:
    contacting a carbon dioxide adsorbent comprising a double salt with an input gas stream containing carbon dioxide, the double salt including a first metal salt and a second metal salt, the first metal salt including CaO, $CaCO_3$, and/or $Ca(OH)_2$, and the second metal salt including $Na_2CO_3$ and/or $Na_2CO_3.H_2O$,
    wherein the carbon dioxide adsorbent does not include MgO, and wherein the Na:Ca mole ratio is greater than or equal to about 0.01 and less than about 0.36, and
    wherein a mole ratio of the second metal to the first metal is greater than or equal to about 0.01 and less than about 0.36.

15. The method of claim 14, wherein the first metal salt comprises CaO.

16. The method of claim 14, wherein the second metal salt comprises $Na_2CO_3$.

17. The method of claim 14, further comprising:
    heat-treating the carbon dioxide adsorbent at a temperature of about 200° C. to about 900° C. to desorb the carbon dioxide.

18. The method of claim 14, wherein the contacting is performed at a temperature of about 500° C. to 650° C.

* * * * *

UNITED STATES PATENT AND TRADEMARK OFFICE
CERTIFICATE OF CORRECTION

PATENT NO. : 9,901,899 B2  
APPLICATION NO. : 14/620761  
DATED : February 27, 2018  
INVENTOR(S) : Hyuk Jae Kwon et al.

Page 1 of 1

It is certified that error appears in the above-identified patent and that said Letters Patent is hereby corrected as shown below:

On the Title Page (72) Inventors should read:  
Hyuk Jae Kwon, Suwon-si (KR); Soon Chul Kwon, Hwaseong-si (KR);  
Hyun Chul Lee, Hwaseong-si (KR); Ki Bong Lee, Seoul (KR);  
Chan Hyun Lee, Seoul (KR); Hee Jin Jang, Seoul (KR)

Signed and Sealed this  
Eighteenth Day of June, 2019

Andrei Iancu  
*Director of the United States Patent and Trademark Office*